United States Patent [19]

Beck et al.

[11] 4,333,923

[45] Jun. 8, 1982

[54] METHOD FOR IMPROVING THE EFFICIENCY OF RUMINANT FEED UTILIZATION

[75] Inventors: James R. Beck, Indianapolis; Joseph A. Yahner, Clinton, both of Ind.

[73] Assignee: Eli Lilly and Company, Indianapolis, Ind.

[21] Appl. No.: 247,673

[22] Filed: Mar. 26, 1981

[51] Int. Cl.$^3$ ............... A61K 35/00; A61K 37/00; A61K 31/335

[52] U.S. Cl. ........................... 424/115; 424/177; 424/279; 426/2

[58] Field of Search .............. 424/115, 279, 177

[56] References Cited

U.S. PATENT DOCUMENTS

| | | | |
|---|---|---|---|
| 3,501,568 | 3/1970 | Haney et al. | 424/115 |
| 3,715,372 | 2/1973 | Stempel et al. | 424/115 |
| 3,839,557 | 10/1974 | Raun | 424/115 |
| 3,937,836 | 2/1976 | Raun | 424/115 |

FOREIGN PATENT DOCUMENTS 10348 4/1980 European Pat. Off. .

OTHER PUBLICATIONS

J. Anim. Sci., 43 (3) (1976) pp. 670–677.
J. Anim. Sci., 51 (1) (1980) pp. 170–179.
J. Anim. Sci., 49 (4) (1979) pp. 1066–1075.
Appl. Environ. Microbiol., 38 (1) (1979) pp. 72–77.

*Primary Examiner*—Donald B. Moyer
*Attorney, Agent, or Firm*—Charles W. Ashbrook; Arthur R. Whale

[57] ABSTRACT

Phthalides enhance propionate production and inhibit methane production in the rumen and are thus useful for improving feed utilization efficiency in ruminant animals.

14 Claims, No Drawings

METHOD FOR IMPROVING THE EFFICIENCY OF RUMINANT FEED UTILIZATION

BACKGROUND OF THE INVENTION

Animals having a developed rumen function utilize the feed which is consumed by first degrading the carbohydrate (the main nutritive portion) to pyruvate. The pyruvate is further metabolized to volatile fatty acid (VFA) derivatives, which include acetate, propionate and butyrate. The animals are capable of producing propionate in the rumen and of absorbing propionate from the gut more efficiently than either acetate or butyrate. One method for improving the efficiency of feed utilization by ruminants therefore involves altering the rumen function to increase propionate production at the expense of acetate and butyrate production.

Another method for improving efficiency involves inhibition of methane production. Methane gas is a product of metabolization in the rumen, and is generally lost through eructation. This represents an energy loss which can be minimized by inhibiting methane formation.

It has now been discovered that certain phthalides are effective in increasing propionate production in animals having a developed rumen function, and also inhibit methane production. The compounds therefore are valuable in improving the efficiency of feed utilization by ruminants.

Phthalides are well known in the art. Several 3-(trichloromethyl)phthalides were synthesized by Fritsch, *Ann.*, 296, 344; *Beilstein*, 18, 20. A number of 6-hydroxy- (and 6-alkoxy)-3-(trichloromethyl)phthalide derivatives have been reported; see *Chem. Abs.*, 61, 11927H et. seq. and 63, 14746E et. seq. Phthalides have been employed in the treatment of plant fungal diseases such as rice blast (Japanese No. 7131350), and as pesticides and pharmaceuticals, (see U.S. Pat. No. 3,342,837). Phthalides have not heretofore been employed in ruminants for improving feed utilization efficiency.

SUMMARY OF THE INVENTION

This invention concerns a method for improving feed utilization efficiency in ruminant animals, and a feedstuff useful for such method. The invention provides a method for improving ruminant feed utilization efficiency which comprises orally administering to a ruminant animal having a developed rumen function a propionate-increasing amount, or a methane-inhibiting amount, of a phthalide having the formula

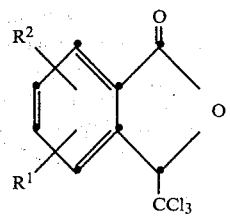

wherein: $R^1$ and $R^2$ independently are hydrogen, hydroxy, $C_1$-$C_3$alkoxy, or $C_1$-$C_3$alkyl.

A preferred method according to the invention employs a compound of the above formula wherein $R^1$ is hydrogen, hydroxy or alkoxy, and $R^2$ is hydroxy, alkoxy or alkyl.

Additionally provided by this invention is a ruminant feedstuff comprising a phthalide propionate enhancer (or methane inhibitor) of the above formula together with a suitable carrier therefor.

DETAILED DESCRIPTION

In the above general formula, $R^1$ and $R^2$ define hydrogen, hydroxy, alkyl and alkoxy groups. The term "$C_1$-$C_3$alkyl" includes groups such as methyl, ethyl and isopropyl, and "$C_1$-$C_3$ alkoxy" refers to groups such as methoxy, ethoxy, and n-propoxy.

The method of this invention is most preferably practiced by employing a compound selected from 5,6-dimethoxy-3-(trichloromethyl)phthalide; 4,6-dihydroxy-3-(trichloromethyl)phthalide; 6-methoxy-3-(trichloromethyl)phthalide; 6-ethoxy-3-(trichloromethyl)phthalide; 6-hydroxy-3-(trichloromethyl)phthalide; 6,7-dimethoxy-3-(trichloromethyl)phthalide; 5-methyl-6-methoxy-3-(trichloromethyl)phthalide and 5-hydroxy-6-ethoxy-3-(trichloromethyl)phthalide.

As already noted, the phthalides employed in the method of this invention are in general well known in the art. They are available from any of several art known synthetic methods. The compounds are most conveniently prepared by reacting trichloroacetaldehyde with a benzoic acid according to the following scheme:

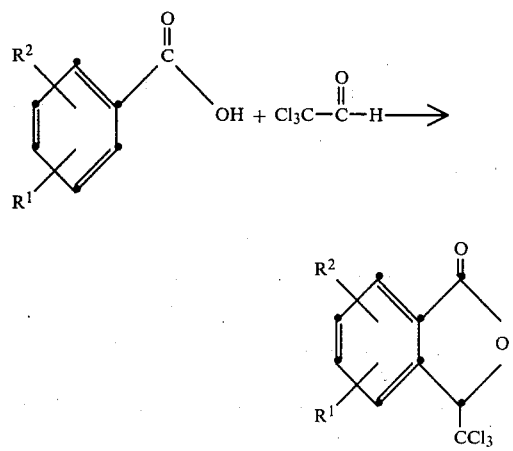

wherein $R^1$ and $R^2$ are as defined above. The reactants can be combined in approximately equimolar quantities, but ideally the acetaldehyde derivative is employed in an excessive amount, for instance about 0.1 to about 1.0 molar excess. The reaction is carried out in a solvent and is catalyzed by the addition of an acid, for instance a mineral acid such as sulfuric acid. The reaction can be conveniently carried out by simply employing the acid catalyst as the reaction solvent. The reaction is normally substantially complete within about 2 to about 48 hours when carried out at a temperature of about 20° to about 100° C. Isolation of the product can be accomplished by simply adding the reaction mixture to ice and water, and extracting the product into a suitable organic solvent such as diethyl ether, or simply collecting the precipitate, if one has formed, by filtration. The product can be purified further if desired by crystallization from common solvents such as ethanol, acetone, methyl ethyl ketone and the like.

The following detailed examples will further illustrate specific aspects of the synthesis of typical phthalides employed in the method of the invention.

EXAMPLE 1

6-Ethoxy-3-(trichloromethyl)phthalide

To a stirred solution of 6.6 g (40 mmoles) of 3-ethoxybenzoic acid in 50 ml. of concentrated sulfuric acid were added dropwise over fifteen minutes 8.0 g (55 mmoles) of trichloroacetaldehyde (chloral). The reaction mixture was stirred for twelve hours at 25° C., and then an additional 8.0 g of chloral were added in one portion and the mixture was stirred for an additional three hours. The reaction mixture was next added to 50 g of ice and 50 ml of water, and the aqueous mixture was extracted several times with diethyl ether. The ethereal extracts were combined, washed with aqueous sodium bicarbonate and then with fresh water, and dried. The solvent was removed by evaporation under reduced pressure to provide an oil. The oil solidified and then was crystallized from ethanol to afford 1.1 g of 6-ethoxy-3-(trichloromethyl)phthalide. m.p. 112°–114° C.

Analysis calc. for $C_{11}H_9Cl_3O_3$: Theory: C, 44.70; H, 3.07; Cl, 35.99. Found: C, 44.54; H, 3.09; Cl, 35.84.

By reacting the appropriately substituted benzoic acid with a haloacetaldehyde according to the procedure of Example 1, the following phthalides were prepared.

EXAMPLE 2

4,6-Dihydroxy-3-(trichloromethyl)phthalide m.p. 100°–102° C.

Analysis calc. for $C_9H_5Cl_3O_4$: Theory: C, 38.13; H, 1.78; Cl, 37.52. Found: C, 37.90; H, 2.08; Cl, 37.68.

EXAMPLE 3

5,6-Dimethoxy-3-trichloromethyl)phthalide m.p. 143°–145° C.

Analysis calc. for $C_{11}H_9Cl_3O_4$: Theory: C, 42.41; H, 2.91; Cl, 34.14. Found: C, 42.62; H, 3.04; Cl, 34.10.

EXAMPLE 4

6-Hydroxy-3-(trichloromethyl)phthalide m.p. 199°–200° C.

Analysis calc. for $C_9H_5Cl_3O_3$: Theory: C, 40.41; H, 1.88. Found: C, 40.54; H, 1.78.

EXAMPLE 5

5-Methyl-6-methoxy-3-(trichloromethyl)phthalide m.p. 128°–130° C.

Analysis calc. for $C_{11}H_9Cl_3O_3$: Theory: C, 44.70; H, 3.07; Cl, 35.99. Found: C, 44.75; H, 2.79; Cl, 36.20.

EXAMPLE 6

6,7-Dimethoxy-3-(trichloromethyl)phthalide m.p. 100°–101° C.

Analysis calc. for $C_{11}H_9Cl_3O_4$: Theory: C, 42.41; H, 2.91; Cl, 34.14. Found: C, 42.66; H, 2.99; Cl, 34.39.

EXAMPLE 7

6-Methoxy-3-(trichloromethyl)phthalide m.p. 134°–135° C.

Analysis calc. for $C_{10}H_7Cl_3O_3$: Theory: C, 42.66; H, 2.51; Cl, 37.78. Found: c, 42.87; H, 2.60; Cl, 37.76.

EXAMPLE 8

5-Hydroxy-6-ethoxy-3-(trichloromethyl)phthalide

To a stirred solution of 16.8 g (80 mmoles) of 3,4-diethoxybenzoic acid in 100 ml. of concentrated sulfuric acid were added dropwise over thirty minutes 16 g (110 mmoles) of chloral. The reaction mixture was stirred at 25° C. for twelve hours. Thin layer chromatographic analysis indicated two components, one of which appeared to be the starting benzoic acid. Six grams of chloral were added to the reaction mixture and stirring was continued for two hours. An additional 10 g of chloral were added and the mixture was stirred for another twelve hours. The reaction mixture was then added to 50 g of ice and 50 g of water, and a solid precipitate formed. The solid product was collected by filtration and then crystallized from ethyl acetate to give 3.3 g of white crystals having a melting point above 260° C. The crystals were dissolved in ethanol and the precipitate which formed was collected, m.p. 143°–144° C. 150 mg. NMR and analysis were consistent for a structure representing 5-hydroxy-6-ethoxy-3-(trichloromethyl)phthalide.

Analysis calc. for $C_{11}H_9Cl_3O_4$: Theory: C, 42.40; H, 2.91; Cl, 34.14. Found: C, 42.45; H, 3.11; Cl, 34.33.

As mentioned above, the phthalides defined herein are effective in causing an increase in the amount of propionate that is produced by metabolism of consumed feed in a developed rumen. The ability of the compounds to cause such increase in propionate production has been demonstrated in standard tests employed to analyze compounds which improve the efficiency with which ruminant animals utilize their feed. A typical test is one which measures the volatile fatty acids produced in a rumen environment.

This test is carried out in vitro in a fermentation flask which mimics the action of the rumen, and the effect of the test is measured by analytical determination of the amounts of acetate, propionate and butyrate in the rumen fluid. The test is carried out as follows.

Rumen fluid is obtained from a steer which has a surgically-installed fistula opening into the rumen. The steer is maintained on the following ration:

| | |
|---|---|
| 40.89% | coarse ground corn |
| 35% | ground corncobs |
| 8.1% | soybean meal (50% protein) |
| 4% | alfalfa meal |
| 10% | molasses |
| 0.65% | urea |
| 0.6% | dicalcium phosphate |
| 0.3% | calcium carbonate |
| 0.3% | salt |
| 0.07% | Vitamin A and $D_2$ premix |
| 0.05% | Vitamin E premix |
| 0.04% | trace mineral premix |

A sample of rumen fluid is strained through four layers of cheesecloth and the eluate is collected in a vacuum bottle. The particulate matter retained by the cheesecloth is resuspended in enough physiological buffer to return it to the original volume of the rumen fluid, and the eluate is strained again. The buffer used is described below:

0.316 g./l. $Na_2HPO_4$
0.152 g./l. $KH_2PO_4$
2.260 g./l. $NaHCO_3$
0.375 g./l. KCl
0.375 g./l. NaCl
0.112 g./l. $MgSO_4$
0.038 g./l. $CaCl_2$
0.008 g./l. $FeSO_4.7H_2O$
0.004 g./l. $MnSO_4$ 0.004 g./l. ZnSO₄.7H₂O
0.002 g./l. CuSO₄.5H₂O
0.001 g./l. CoCl₂

This buffer is described by Cheng et al., *J. Dairy Sci.* 38, 1225 (1955).

The two eluates are pooled in a separatory funnel and allowed to stand until particulate matter separates to the top. The clear layer is then diluted 1:1 with the same buffer, and adjusted to pH 7.0 with HCl or NaOH.

Ten ml. of the diluted rumen fluid prepared above is placed in a 25 ml flask with 80 mg of the same feed shown above. The compound to be tested is added to the feed, in sufficient quantity to give the concentrations of test compound in the flask which are listed in the table below. Five mg of soybean protein is also added to each flask. Three replicate flasks are used per treatment.

Two sets of three untreated control flasks each are also prepared. One set of control flasks is incubated for 16 hours at 38° C. with the test flasks. The other set of three untreated control flasks are zero-time controls, to which 2 ml of 25 percent metaphosphoric acid is added as soon as the flasks are prepared to stop the fermentation.

Fermentation in the incubated test and control flasks is stopped at the end of 16 hours by addition of 2 ml of 25 percent metaphosphoric acid to each flask.

All of the samples are allowed to settle, and the supernatant is analyzed by gas chromatographic methods for acetate, propionate, and butyrate.

The analysis for each volatile fatty acid (VFA) found in the zero-time controls is subtracted from the analyses of the untreated controls and of the test flasks. The resulting values reflect the amount of each VFA produced during the 16-hour fermentation period. The values obtained from the replicate flasks on each treatment are averaged, and the results of different tests at the same rates are also averaged.

The data are reported as the ratio of VFA's produced in treated flasks to VFA's produced in untreated control flasks. Controls thus have a value of 1.00 for each of the components. This method of reporting the data shows most clearly the results of the changes in the chemistry of the rumen. Total VFA production is also reported in the same manner.

Table I below reports test results of representative compounds to be employed in the method of this invention.

TABLE I

| Compound of Example No. | Rate mcg./ml. | Acetate | Propionate | Butyrate | Total VFA |
| --- | --- | --- | --- | --- | --- |
| Control | | 1.00 | 1.00 | 1.00 | 1.00 |
| 1 | 10 | 0.81 | 1.61* | 0.98 | 1.25 |
| | 10 | 0.85 | 1.34* | 1.12* | 0.92 |
| 2 | 10 | 0.88 | 1.17* | 1.00 | 0.80 |
| | 10 | 0.85 | 1.27* | 0.99 | 0.88 |
| | 10 | 0.73 | 1.43* | 1.27 | 0.82 |
| | 10 | 0.81 | 1.42* | 1.21* | 0.81 |
| 3 | 10 | 0.82 | 1.20* | 1.10 | 0.81 |
| | 10 | 0.82 | 1.33* | 0.99 | 0.84 |
| | 10 | 0.82 | 1.26 | 1.22 | 0.82 |
| | 10 | 0.80 | 1.42* | 1.25* | 0.73 |
| 4 | 10 | 1.04 | 0.95 | 1.03 | 0.92 |
| | 10 | 0.90 | 1.10* | 1.07 | 0.88 |
| | 10 | 0.86 | 1.08 | 1.32* | 0.68 |
| | 10 | 0.75 | 1.68* | 0.87 | 0.72 |
| 5 | 10 | 0.82 | 1.13* | 1.19* | 0.96 |
| | 10 | 0.80 | 1.19* | 1.03 | 1.02 |
| 6 | 10 | 0.96 | 1.16* | 0.78 | 0.87 |
| | 10 | 0.81 | 1.22* | 1.24* | 0.87 |

TABLE I-continued

| Compound of Example No. | Rate mcg./ml. | Acetate | Propionate | Butyrate | Total VFA |
| --- | --- | --- | --- | --- | --- |
| 7 | 10 | 0.76 | 1.25* | 1.12 | 0.97 |
| | 10 | 0.74 | 1.20* | 1.37* | 0.87 |
| | 10 | 0.94 | 1.08 | 0.96 | 0.89 |
| 8 | 10 | 0.84 | 1.17* | 1.10 | 0.79 |
| | 10 | 0.86 | 1.39* | 0.83 | 0.92 |
| | 10 | 0.71 | 1.45* | 1.29 | 0.82 |
| | 10 | 0.80 | 1.40* | 1.27* | 0.75 |

*indicates that the reported figure differs significantly from control(2-tailed L.S.D. test, P < 0.01).

An additional in vitro test was carried in continuous fermentation flasks which mimic the action of the rumen over a long period of time. Each flask was a gas-tight container having liquid inlet ports, solid inlet ports, sampling ports and gas exit tubes leading to rubber bladders which receive the gases produced by the fermentation. The liquid volume in each flask was controlled at 500 ml by a stand pipe leading to a liquid collection vessel. The temperature of the flasks was controlled at 38°–40°. Each flask was gently stirred by a magnetic stirrer.

Each experiment was started by adding to a flask 500 ml of strained rumen fluid obtained from a fistulated steer which had been fed the same diet being used in the test. The effluent collection flask was pre-charged with 50 ml of dilute metaphosphoric acid, to stop fermentation in the liquid overflowing from the flask. The flask was sealed, and the gas collection bladders were attached.

Liquid was added to each flask continuously by dripping into it a liter per day of pH 6.8–7.0 buffer having the following composition:

| Sodium hydrogen phosphate | 2.2 g/liter |
| --- | --- |
| Magnesium chloride | 0.036 |
| Sodium bicarbonate | 5.9 |
| Potassium chloride | 0.34 |
| Sodium chloride | 0.28 |
| Urea | 1.0 |
| Calcium chloride | 0.024 |

A 10 g addition of the appropriate feed was added twice daily through the feeding port to each flask. After each feeding, the gas outlet port was closed off and the flask was flushed with carbon dioxide.

Each day, the effluent liquid was collected and analyzed, and the gas which left the flask was collected and analyzed.

The usual practice was to operate each flask for 4 days without any treatment compound added to the feed. After the 4-day period of equilibration, analysis of the liquid and gaseous effluents was started, and the flask was operated, without any addition of treatment compound, until the analytical data became relatively constant. The addition of treated feed to the flask was started at that time, and the flask was operated on treated feed for a minimum of 7 days.

The compound was added to the feed in amounts suitable to give the concentration of compound in the 500 ml liquid volume of the flask which is shown in the tables below.

Acetate, propionate and butyrate data were obtained on the effluent liquid from each flask, and are expressed as described in Test 1. The effluent gas from each flask was analyzed for methane, and methane inhibition data are expressed below as the amount of methane produced by the test fermenters, as a percentage of the amount of methane produced by untreated control flasks. As mentioned above, methane inhibition also contributes to more efficient feed utilization in ruminants by diverting the acetate to usable energy rather than to methane which is expelled.

In most tests, 2 flasks were used for each treatment level of each compound, and the data from both flasks from all treatment days were pooled and averaged.

The table below reports data obtained from tests in which the full flasks were fed a diet consisting of 50% hay and 50% of the mixed ration described in Test 1 above.

TABLE II

| Compound of Example No. | Rate mcg./ml. | Acetate | Propionate | Butyrate | Total VFA | Methane Production |
|---|---|---|---|---|---|---|
| Control | | 1.00 | 1.00 | 1.00 | 1.00 | 1.00 |
| 7 | 5 | 0.82 | 1.38 | 1.50 | 0.83 | 0.32 |
| 7 | 5 | 0.84 | 1.29 | 1.54 | 0.90 | 0.49 |

The above data illustrate the effectiveness of the phthalides defined herein in beneficially changing the rumen fermentation in ways which result in more efficient use of a ruminant animal's food. Accordingly, the compounds are valuable in a method of increasing the efficiency of feed utilization by ruminant animals having a developed rumen function, which method comprises the oral administration to such animals of a propionate increasing, or methane inhibiting, amount of a compound defined herein.

The method of this invention is useful to all ruminant animals which have a developed rumen function, of which the most economically important are cattle, sheep and goats. Young ruminants, especially those still unweaned, function as monogastric animals. As the young animals begin to eat solid food, containing cellulose, starch and other carbohydrates, the function of the rumen begins to develop, and its micropopulation begins to increase. After the animal has eaten solid food for a time, its rumen develops its full function and continues to operate throughout the animal's life.

It will be understood that the usefulness of the method is not limited to young animals, or those which are being fattened. When the method of this invention is applied to adult animals, such as milk cows or breeding stock, its benefit is seen as reducing the food consumption necessary to maintain weight and animal performance.

The method of this invention is carried out by administering at least the amount of a compound of this invention necessary to increase production of propionates in the rumen, or to inhibit the production of methane. Both functions may be and usually are attained by the same administration.

The amount of compound to be administered according to this invention is usually in the range of from about 0.1 mg of compound per kg of body weight per day, to about 6 mg/kg/day. The preferred range of administration rates is from about 0.25 mg/kg/day to about 3 mg/kg/day. Those skilled in the animal husbandry art will understand that the optimum administration rate necessarily varies, depending on the condition the animals are in, the animals' age, the type of food they are eating, and the purpose for which the animals are maintained.

The nature of the method of this invention requires that the compound must be orally administered, and must be administered in such a manner that the compound is present in the rumen. One way to administer the compound to accomplish the goal, especially in animals which are on pasture, is to administer the compound in the form of a sustained release bolus. Such boluses can be made as tablets, ideally with a means to delay the dissolution of the compound over a prolonged period of time. Boluses may be made to release the compound steadily over long periods of time, even 100 days or more. A number of polymeric substances have been used to prepare such boluses; particularly effective polymers are the copolymers of polylactic and polyglycolic acids. It is necessary to retain such a bolus in the rumen of the animal, so that the bolus is not carried out of the digestive tract. Such boluses are easily retained in the rumen by making them of a high-density substance, such as by mixing metal particles into the composition, or by providing wings which open in the rumen and make the bolus too large to get through the opening into the animal's omasum. Such boluses should release from about 0.1 mg of compound per kg of body weight per day to about 6 mg/kg/day, preferably from about 0.25 to about 3 mg/kg/day.

Mineral blocks are another advantageous form in which to administer the compounds, particularly to animals on pasture or range. Such blocks are usually supplied to ruminants. The usual blocks are highly compressed forms of physiologically-desirable salts and nutritive substances, which generally include phosphates, carbonates, halides, calcium salts, trace elements such as zinc, cobalt, manganese and the like, vitamins, stearoids, and lubricants and binders to assist in compression. Mineral blocks are old in the animal husbandry art, of course. The addition of a compound of this invention, however, provides novel blocks which are important embodiments of the present invention. The compounds should be added to the blocks in concentrations from about 0.05% to about 7%, preferably from about 0.1% to about 4%.

The compounds may also be mixed into protein blocks for administration to animals. Such blocks are known, and consist of a mixture of molasses and urea, with other protein sources optionally added as well, and are supplied to ruminants to be eaten at will. Protein blocks containing a compound of this invention should contain from about 0.025% to about 3%, preferably from about 0.05% to about 2%.

It is possible, of course, to administer a compound of this invention in the form of orally-administered pharmaceutical dosage forms, such as tablets, capsules and the like. It is obviously more expensive and less convenient to administer such compositions than to administer the compound in the form of a bolus or mineral block, and accordingly such dosage forms are not preferred.

The most preferred form in which to administer compounds of this invention is as additives to the animals' feed. Accordingly, feed compositions which contain the compounds defined herein are novel themselves, and are extremely important embodiments of the invention.

Animal feed compositions are usually prepared stagewise. First, the compound is mixed with inert ingredients to prepare a feed premix, which is the form in which the compound is shipped from the original manufacturer to a local feed mill. Premixes may be either liquid or solid, and may contain from about 1% to about 90% of the compound. The inert ingredients of a feed premix are not at all critical, and may be any of the conventionally-used physiologically-acceptable carriers. Liquid carriers include, for example, glycols such as polyethylene glycols of various molecular weights and propylene glycol, inert oils including vegetable oils and refined mineral oil, and physiologically-acceptable alcohols such as ethanol. Solid premix carriers include, for example, vermiculite, diatomaceous earth, physiologically-acceptable clays such as attapulgite and montmorillonite, and granulated or powdered feed components such as cracked corn, soybean meal, alfalfa meal, rice hulls, crushed corncobs, cracked wheat or oats and all sorts of waste materials of grain processing. Such ingredients of solid feed premixes are often granulated, pelleted or otherwise treated, as with dusting oils, to assure that the feed premix is not dusty and remains homogeneous.

The following are typical examples of feed premix compositions which are embodiments of the present invention.

| I. | |
|---|---|
| ground oats | 94% |
| propylene glycol | 2 |
| lignin | 3 |
| compound of Example 1 | 1 |
| II. | |
| yellow corn | 24% |
| ground corn cobs | 25 |
| mineral oil | 1 |
| compound of Example 2 | 50 |
| III. | |
| soybean meal | 10% |
| compound of Example 6 | 90 |
| IV. | |
| wheat middlings | 52.95% |
| bentonite | 5 |
| corn oil | 2 |
| ground limestone | 20 |
| ethoxyquin | 0.05 |
| compound of Example 3 | 20 |
| V. | |
| polyethylene glycol | 90% |
| compound of Example 8 | 9 |
| polyoxyethylene ester | 1 |
| VI. | |
| dicalcium phosphate | 68% |
| mineral oil | 2 |
| compound of Example 7 | 30 |
| VII. | |
| vermiculite | 33% |
| cottonseed oil | 2 |
| compound of Example 4 | 65 |
| VIII. | |
| rice hulls | 22.5% |
| molasses | 2.5 |
| compound of Example 3 | 75 |
| IX. | |
| mineral oil | 90% |
| polyglycerol ester | 5 |
| compound of Example 7 | 5 |
| X. | |
| ground corn cobs | 91% |
| soybean oil | 1 |
| compound of Example 5 | 8 |

A second stage in the manufacture of animal feeds is the feed supplement or concentrate. Such supplements are compositions containing a compound of this invention, mixed with nutritive substances such as minerals, inorganic salts, trace elements and vitamins. Supplements are often mixed by diluting a feed premix with other constituents, and are often made up by local feed mills for use by large livestock operations. A supplement may be used in the manufacture of complete mixed feed compositions containing a compound of this invention, or may be simply poured over unmedicated feed in the feed troughs or feed bunkers. The concentration of compounds in supplements varies widely, depending on the amount of the supplement to be fed to each animal. In general, concentrations are from about 0.0015% to about 0.93%, preferably from about 0.0035% to about 0.46%. Examples of feed supplement compositions containing compounds of this invention are the following:

| I. | |
|---|---|
| ground corn cobs | 38.57% |
| soybean meal | 25.0 |
| ground corn | 20.0 |
| ground oats | 10.0 |
| molasses | 2.5 |
| salt | 0.4 |
| vitamin premix | 1.1 |
| animal fat | 1.5 |
| compound of Example 1 | 0.93 |
| II. | |
| soybean meal | 66.897% |
| milo | 25.5 |
| dicalcium phosphate | 2.1 |
| limestone | 1.2 |
| salt | 1.6 |
| molasses | 2.1 |
| trace minerals and vitamin premix | 0.6 |
| compound of Example 7 | 0.003 |
| III. | |
| milo | 81.9% |
| monosodium phosphate | 8.8 |
| salt | 5.1 |
| molasses | 2.1 |
| trace minerals and vitamin premix | 2.0 |
| compound of Example 3 | 0.1 |
| IV. | |
| soybean meal | 64.2985% |
| biuret | 10.0 |
| dicalcium phosphate | 4.2 |
| sodium tripolyphosphate | 2.1 |
| sulfur | 0.4 |
| molasses | 6.0 |
| salt | 12.8 |
| trace mineral premix | 0.2 |
| compound of Example 5 | 0.0015 |
| V. | |
| soybean meal | 49.59% |
| alfalfa meal | 24.8 |
| urea | 12.4 |
| dicalcium phosphate | 2.5 |
| ground limestone | 7.4 |
| salt | 2.5 |
| vitamin premix | 0.8 |
| compound of Example 4 | 0.01 |
| VI. | |
| soybean meal | 89.55% |
| dicalcium phosphate | 10.0 |
| compound of Example 8 | 0.45 |
| VII. | |
| soybean meal | 70.78% |
| ground corn | 15.4 |
| soybean oil | 5.0 |
| dicalcium phosphate | 4.78 |
| calcium carbonate | 0.96 |
| salt | 0.76 |
| vitamin and trace mineral premix | 2.1 |
| compound of Example 2 | 0.22 |
| VIII. | |
| soybean meal | 10.75% |

| -continued | |
|---|---|
| urea | 20.0 |
| dicalcium phosphate | 16.0 |
| calcium carbonate | 24.0 |
| salt | 20.0 |
| sodium bicarbonate | 2.0 |
| trace mineral and vitamin premix | 7.2 |
| compound of Example 6 | 0.05 |

It will be understood by those skilled in the art of animal husbandry that ruminant animal feeds which contain compounds defined herein are novel and are extremely useful in improving the efficiency of the utilization of food by such animals. Feeds for ruminant animals are usually and preferably cereal-based, adapted to the needs of such animals. The usual dry or slurried ruminant feeds, based on grains such as wheat, oats, barley, corn and the like, are treated with the phthalides of this invention just as animal feeds have long been routinely treated with medicaments in the practice of the animal husbandry art. Such feeds routinely are composed of the basic grains, and are further supplemented with vitamins, minerals, inorganic salts and other important nutritive substances to assure that the ruminant animals are properly nourished. Feed should contain from about 5 parts per million (ppm.) to about 500 ppm. of the compound; preferable feeds should contain from about 10 ppm. to about 300 ppm. For example, the following are typical feed compositions making use of compounds of this invention.

| I. | |
|---|---|
| chopped alfalfa | 54.88% |
| sorghum grain | 36.20 |
| soybean meal | 4.10 |
| urea/grain mixture, 70% protein | 3.60 |
| dicalcium phosphate | 0.90 |
| trace mineralized salt | 0.23 |
| vitamin supplement | 0.09 |
| compound of Example 3 | 5 ppm |
| II. | |
| ground sorghum | 60.0% |
| alfalfa meal | 15.0 |
| cottonseed hulls | 15.0 |
| cottonseed meal | 8.5 |
| salt | 1.0 |
| ground limestone | 0.5 |
| compound of Example 1 | 250 ppm |
| III. | |
| milo silage | 58.2% |
| sorghum silage | 28.1 |
| soybean meal | 8.0 |
| rolled grain sorghum | 5.0 |
| dicalcium phosphate | 0.1 |
| calcium carbonate | 0.2 |
| salt | 0.2 |
| soybean oil | 0.1 |
| vitamin and antibiotic premix | 0.1 |
| compound of Example 5 | 10 ppm |
| IV | |
| ground corn cobs | 11.32% |
| corn | 75.00 |
| soybean meal | 9.00 |
| molasses | 3.10 |
| urea | 0.09 |
| ground limestone | 0.95 |
| salt | 0.50 |
| trace mineral and vitamin premix | 0.04 |
| compound of Example 8 | 25 ppm |
| V. | |
| wheat | 44.54% |

| -continued | |
|---|---|
| corn cobs | 45.00 |
| cane molasses | 3.00 |
| soybean meal | 6.40 |
| dicalcium phosphate | 0.65 |
| limestone | 0.38 |
| trace minerals | 0.03 |
| compound of Example 6 | 50 ppm |
| VI. | |
| barley | 83.70% |
| soybean meal | 13.15 |
| ground limestone | 1.15 |
| dicalcium phosphate | 0.80 |
| salt | 0.50 |
| vitamin and trace mineral premix | 0.70 |
| compound of Example 7 | 500 ppm |
| VII. | |
| ground timothy hay | 15% |
| ground alfalfa hay | 15 |
| cracked corn | 50 |
| soybean oil meal | 10 |
| molasses | 9 |
| trace mineralized salt and vitamin premix | 1 |
| compound of Example 2 | 100 ppm |

The method of this invention can be practiced by administering a phthalide as defined herein to a ruminant in combination with another feed efficiency enhancing agent or growth promoter. Many such agents are known and several are used commercially in the beef industry. Such agents include the polyethers such as monensin, salinomycin, lasalocid and the like, as well as the glycopeptides such as avoparcin, actaplanin and the like. It is contemplated that a preferred method of practicing this invention will involve administering to a ruminant a phthalide as defined herein in combination with monensin in a weight ratio of about 1 to 10 parts phthalide to about 10 to 1 parts monensin.

We claim:

1. A method of increasing the efficiency of feed utilization by ruminant animals having a developed rumen function which comprises the oral administration to such animals of a propionate-increasing amount or a methane-inhibiting amount of a compound having the formula

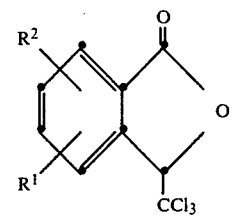

wherein: $R^1$ and $R^2$ independently are hydrogen, hydroxy, $C_1$-$C_3$alkoxy, or $C_1$-$C_3$alkyl.

2. The method of claim 1 employing a compound wherein $R^1$ is hydrogen, hydroxy or alkoxy.

3. The method of claim 2 employing a compound wherein $R^2$ is hydroxy, alkoxy or alkyl.

4. The method of claim 3 employing a compound wherein $R^1$ is hydrogen and $R^2$ is methoxy, ethoxy or hydroxy.

5. The method of claim 3 employing a compound wherein $R^1$ is hydroxy and $R^2$ is hydroxy, methoxy or ethoxy.

6. The method of claim 3 employing a compound wherein $R^1$ and $R^2$ independently are methoxy or ethoxy.

7. The method of claim 1 wherein the phthalide is administered in combination with a polyether or glycopeptide feed efficiency enhancing agent.

8. The method of claim 7 wherein the phthalide is administered in combination with monensin.

9. A ruminant feedstuff comprising a propionate-increasing or methane-inhibiting amount of a compound defined in claim 1 together with a carrier.

10. The feedstuff of claim 9 wherein the amount of compound employed is from about 5 ppm to about 500 ppm.

11. The feedstuff of claim 10 wherein the amount of compound employed is from about 10 ppm to about 300 ppm.

12. The feedstuff of claim 11 employing a compound wherein $R^1$ is hydrogen and $R^2$ is hydroxy, methoxy or ethoxy.

13. The feedstuff of claim 11 employing a compound wherein $R^1$ is hydroxy and $R^2$ is hydroxy, methoxy or ethoxy.

14. The feedstuff of claim 11 employing a compound wherein $R^1$ and $R^2$ independently are methoxy or ethoxy.

* * * * *